United States Patent
Jow et al.

(10) Patent No.: US 7,265,296 B2
(45) Date of Patent: Sep. 4, 2007

(54) FLAME RETARDANT PLENUM CABLE

(75) Inventors: Jinder Jow, Singapore (SG); Jeffrey M. Cogen, Flemington, NJ (US)

(73) Assignee: Union Carbide Chemicals & Plastics Technology Corporation, Danbury, CT (US)

(*) Notice: Subject to any disclaimer, the term of this patent is extended or adjusted under 35 U.S.C. 154(b) by 0 days.

(21) Appl. No.: 10/565,914

(22) PCT Filed: May 5, 2005

(86) PCT No.: PCT/US2005/015618

§ 371 (c)(1),
(2), (4) Date: Jan. 24, 2006

(87) PCT Pub. No.: WO2005/119704

PCT Pub. Date: Dec. 15, 2005

(65) Prior Publication Data

US 2006/0207785 A1    Sep. 21, 2006

Related U.S. Application Data

(60) Provisional application No. 60/568,317, filed on May 5, 2004.

(51) Int. Cl.
*H01B 7/00* (2006.01)
(52) U.S. Cl. .............. 174/110 R; 174/120 R; 174/120 SC
(58) Field of Classification Search .......... 174/36, 174/110 R, 113 R, 120 R, 120 SC
See application file for complete search history.

(56) References Cited

U.S. PATENT DOCUMENTS

| 3,378,628 | A | * | 4/1968 | Garner | 174/112 |
| 5,162,609 | A | * | 11/1992 | Adriaenssens et al. | 174/34 |
| 5,462,803 | A | * | 10/1995 | Wessels | 428/380 |
| 5,670,748 | A | * | 9/1997 | Gingue et al. | 174/120 R |
| 5,841,072 | A | * | 11/1998 | Gagnon | 174/110 F |
| 5,936,205 | A | * | 8/1999 | Newmoyer | 174/113 R |
| 6,255,594 | B1 | * | 7/2001 | Hudson | 174/121 A |
| 6,339,189 | B1 | * | 1/2002 | Caimi | 174/36 |
| 6,392,152 | B1 | * | 5/2002 | Mottine et al. | 174/110 PM |
| 2003/0019655 | A1 | * | 1/2003 | Gagnon | 174/105 R |

FOREIGN PATENT DOCUMENTS

DE   4300795 A1 * 7/1994
DE   WO98/02889 A * 1/1998

* cited by examiner

*Primary Examiner*—William H. Mayo, III

(57) ABSTRACT

The present invention is a flame retardant cable having an insulated conductor and at least two insulation layers. The cable demonstrates a composite dielectric constant less than or equal to about 2.6 and a composite dissipation factor less than or equal to 0.005 even though one of the insulation layers has a dielectric constant greater than 2.6 or a dissipation factor greater than 0.005. The presently invented cable is achieved with a non-halogenated polyolefin as an insulation layer polymer, where the polyolefin having relatively poor dielectric/dissipative properties and the insulation layer composition being substantially free of halogenated or antimony trioxide flame retardant additives.

7 Claims, 1 Drawing Sheet

FLAME RETARDANT PLENUM CABLE

CROSS-REFERENCE TO RELATED APPLICATIONS

PCT/US05/15618, filed May 5, 2005, is a Box VI priority application 60/568,317 filed on May 5, 2004.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

The invention relates to flame retardant cable for telecommunications. More particularly, the invention is directed to an insulated conductor having at least two insulation layers, a composite dielectric constant less than or equal to about 2.6, and a composite dissipation factor less than or equal to about 0.005. Telecommunications cable prepared with the insulated conductors is particularly well-suited for use in plenum spaces of air circulation systems.

In the construction of buildings, it is extremely important to use materials which resist the spread of flame and the generation and spread of smoke in case of fire. Accordingly, it is important to select and install telecommunications cable meeting these material requirements.

Conventional designs of telecommunications cable for plenum chambers of air circulation systems generally use polyvinyl chloride or fluoropolymers as jacketing materials. Also, most plenum cable insulation development has focused on improving flame retardance and reducing smoke generation using expensive fluorinated ethylene polymer ("FEP") or polyolefins having high levels of flame-retardant or smoke-suppressing additives. Unfortunately, the additives degrade the dielectric properties of the polyolefins. Also, when the additives are halogenated, they generate corrosive gases during combustion.

TIA/EIA 568A standards set electrical requirements for category 5 and 5e cables, such as impedance, attenuation, return loss and crosstalk requirements for any given conductor pair in a frequency range of 0.772 to 100 MHz. 100 meters of cable are used for this test. Impedance should not be less than 85 at 0.772 MHz and no more than 115 at 100 MHz. Return loss should be no less than 17 to 25 dB, depending on the testing frequency of 0.772 to 100 MHz. Attenuation should not be higher than 5.8 to 22 dB, depending on testing frequency of 0.772 MHz to 100 MHz.

Impedance and attenuation are important electrical properties. Impedance is the resistance to signal transmission along the length of the cable. The impedance of cable is controlled by conductor diameter and its properties, type of insulation used and its thickness, and tightness with which individual pairs are twisted. Thicker cables give higher impedance. But if insulation is too thick, the cable impedance can exceed the maximum desired value.

Attenuation is the reduction in signal strength over the distance the signal is transmitted. Conductor and insulation are the major contributors to the cable attenuation. The larger conductor or lower resistance gives lower attenuation. The greater insulation thickness also gives lower attenuation.

With a given cable design, the desired dielectric properties of insulation are to have dielectric constant (DC) no more than 2.6 and dissipation factor (DF) no more than 0.005 at 1 MHz, per ASTM D 1531 test method, to meet Category 5/5e electrical requirements on cables.

The NFPA 262 test is a fire test method to determine flame propagation distance and optical smoke density for electrical and optical-fiber cables intended to be installed in ducts, plenums, and other spaces used to transport environmental air without the cable enclosed in raceways. Cables are placed in a cable tray with 25-foot long cables covering the entire tray width of 11.25 inches. An ignition burner flame (88 kW) is applied to the one end of the cable tray with an air velocity of 240 ft/min. The test duration is 20 minutes. The cable will be considered as a pass if the flame spread is no more than 5 ft., the peak smoke is no more than 0.5, and the average smoke is no more than 0.15. A cable is flame retardant if it meets the latter criteria.

U.S. Pat. No. 5,462,803 describes a cable with conductor with fluoropolymer surrounding a conductor and an outer layer of polyvinyl chloride.

U.S. Pat. No. 5,563,377 describes using an inner layer of inexpensive "flame retardant polyolefin" and an outer layer containing FEP. Chlorinated, brominated or metal additives are used to impart flame retardancy to the polyolefin.

Canadian Application 2,238,596 describes a foamed flame retardant inner layer made from a polyolefin and flame-retardant additives.

U.S. Pat. No. 5,670,748 to Gingue, et al. describes a conductor surrounded by a foamed layer of polyolefin or polyurethane and an outer layer of halogenated material.

BRIEF SUMMARY OF THE INVENTION

For a flame retardant cable, it has been surprisingly found that an insulated conductor, having at least two insulation layers, a composite dielectric constant less than or equal to about 2.6, and a composite dissipation factor less than or equal to about 0.005, can be prepared even though one of the insulation layers has a dielectric constant greater than 2.6 or a dissipation factor greater than 0.005.

For an insulated conductor with two layers, the composite dielectric constant, $\varepsilon_t$, is defined by:

$$\varepsilon_t = \frac{\varepsilon_1 \varepsilon_2 \ln\left(\frac{r_2}{r_0}\right)}{\varepsilon_2 \ln\left(\frac{r_1}{r_0}\right) + \varepsilon_1 \ln\left(\frac{r_2}{r_1}\right)}$$

where $\varepsilon_1$ and $\varepsilon_2$ are the dielectric constants of the inner and outer insulation layers, respectively, and $r_0$ is the radius of the conductor; $r_1$ is the sum of $r_0$ and the thickness of the inner insulation layer; and $r_2$ is the sum of $r_1$ plus the thickness of the outer insulation layer.

The composite dissipation factor (or tan delta) is defined as:

$$\tan \delta_t = \frac{\frac{\tan \delta_1}{\varepsilon_1} \ln\left(\frac{r_1}{r_0}\right)}{[\tan \delta_1^2 + 1]} + \frac{\frac{\tan \delta_2}{\varepsilon_2} \ln\left(\frac{r_2}{r_1}\right)}{[\tan \delta_2^2 + 1]}}{\frac{\frac{1}{\varepsilon_1} \ln\left(\frac{r_1}{r_0}\right)}{[\tan \delta_1^2 + 1]} + \frac{\frac{1}{\varepsilon_2} \ln\left(\frac{r_2}{r_1}\right)}{[\tan \delta_2^2 + 1]}}$$

where $\tan \delta_1$ and $\tan \delta_2$ are the dissipation factors of the inner and outer insulation layers, respectively.

It has also been surprisingly found that an insulated conductor, having a composite dielectric constant less than or equal to about 2.6 and a composite dissipation factor less than or equal to about 0.005, can be prepared with a non-halogenated polyolefin as an insulation layer polymer, where the polyolefin having relatively poor dielectric/dissipative properties and the insulation layer composition being substantially free of halogenated or antimony trioxide flame retardant additives.

DETAILED DESCRIPTION OF THE INVENTION

Figure 1:
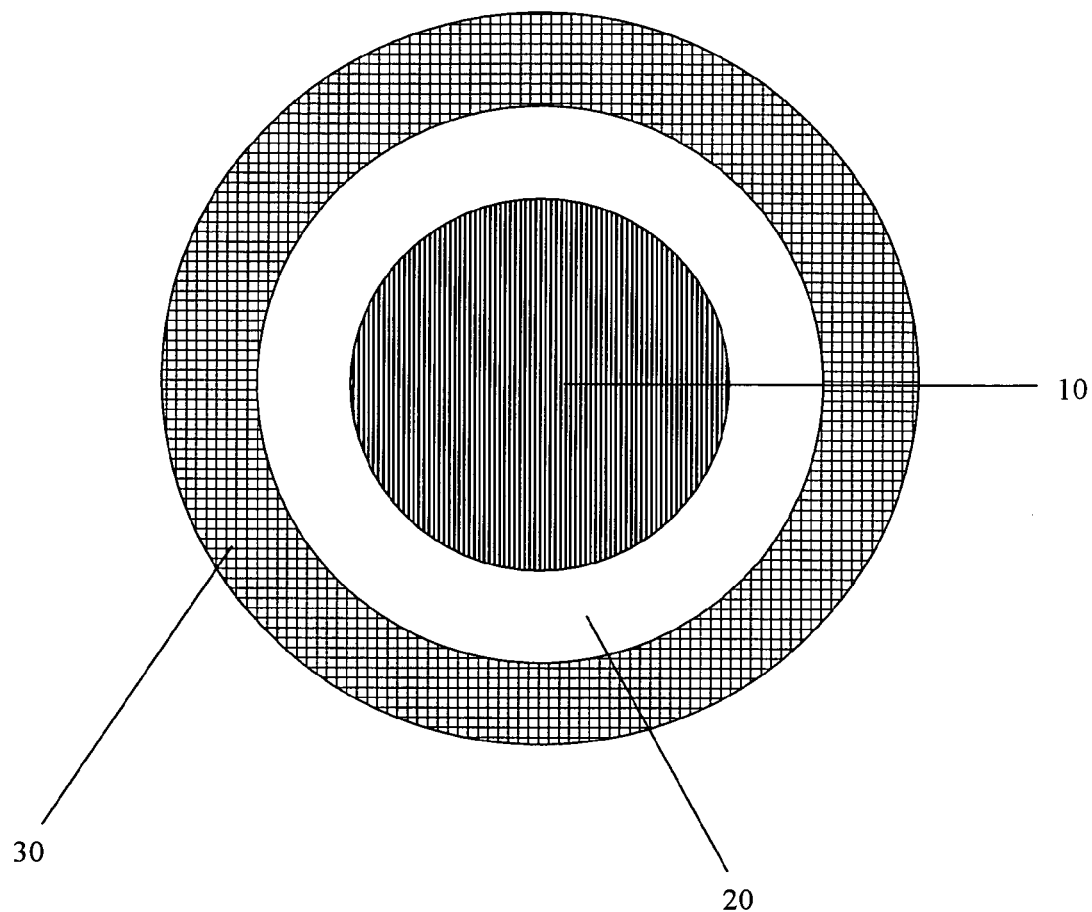
FIG. 1 is a cross-section of a flame retardant cable according to the present invention, having an insulated conductor 10, an inner insulation layer 20, and an outer insulation layer 30.

The flame retardant cable of the present invention includes an insulated conductor, which comprises a conductor, an inner insulation layer surrounding the conductor, and an outer insulation layer surrounding the inner insulation layer. The insulated conductor has a composite dielectric constant of less than or equal to about 2.6 and a composite dissipation factor of less than or equal to about 0.005. The inner insulation layer or the outer insulation layer has a dielectric constant greater than about 2.6, a dissipation factor greater than about 0.005, or both.

In a preferred embodiment, a first polymeric composition for preparing the inner insulation layer comprises a first non-halogenated polymer and being substantially-free of halogenated flame retardant additives or antimony oxide and a second polymeric composition for preparing the outer insulation layer comprises a second non-halogenated polymer and being substantially-free of halogenated flame retardant additives or antimony oxide.

Examples of non-halogenated polyolefins useful in the present invention include polyethylene polymers, polypropylene polymers, ethylene terpolymer, ethylene propylene diene terpolymers (EPDM) or ethylene-propylene rubbers.

Polyethylene polymer, as that term is used herein, is a homopolymer of ethylene or a copolymer of ethylene and a minor proportion of one or more alpha-olefins having 3 to 12 carbon atoms, and preferably 4 to 8 carbon atoms, and, optionally, a diene, or a mixture or blend of such homopolymers and copolymers. The mixture can be a mechanical blend or an in situ blend. Examples of the alpha-olefins are propylene, 1-butene, 1-hexene, 4-methyl-1-pentene, and 1-octene. The polyethylene can also be a copolymer of ethylene and an unsaturated ester such as a vinyl ester (e.g., vinyl acetate or an acrylic or methacrylic acid ester) or a copolymer of ethylene and a vinyl silane (e.g., vinyltrimethoxysilane and vinyltriethoxysilane). A third comonomer can be included, e.g., another alpha-olefin or a diene such as ethylidene norbornene, butadiene, 1,4-hexadiene, or a decyclopentadiene.

Ethylene/propylene/diene terpolymers are generally referred to as an EPDM and ethylene/propylene copolymers are generally referred to as EPRs. For EPDM, the third comonomer can be present in an amount of 1 to 15 percent by weight based on the weight of the copolymer and is preferably present in an amount of 1 to 10 percent by weight. It is preferred that the copolymer contains two or three comonomers inclusive of ethylene.

As used herein, a halogen is defined according to the Periodic Table to include fluorine, chlorine, bromine, iodine, and astatine. Therefore, as used herein, non-halogenated polymer polyolefins excludes polyolefins which are substituted with fluorine, chlorine, or bromine in amounts which render the polyolefin flame retardant. As such, fluorinated ethylene polymers are excluded.

As used herein, substantially free of halogenated flame retardant additives or antimony trioxide means that a halogenated flame retardant additive or antimony trioxide is not present in an amount sufficient to impart flame retardancy to an insulation layer prepared from the insulation composition. In a preferred aspect, a halogenated flame retardant additive or antimony trioxide is not present at all or only in trace amounts.

Examples of non-halogenated flame retardant additives which can be used with the present invention include ethylene diamine phosphate, melamine, melamine pyrophosphate, melamine phosphate, ammonium polyphosphate, melamine polyphosphate, calcium carbonate, talc, clay, organo-modified clay, calcium hexaborate, alumina, titanium oxides, carbon nanotubes, zinc borate, wollastonite, mica, silicone polymers, phosphate esters, hindered amine stabilizers, melamine octomolybdate, ammonium octomolybdate, expandable graphite, frit, hollow glass beads and mixtures thereof.

In this aspect of the invention, the outer insulation layer will have excellent flame retardancy and the inner insulation layer will have excellent electrical properties. Neither insulation layer should generate smoke above desirable levels. The outer insulation layer should have preferably 100 to 300 parts of flame retardant additive per hundred parts by weight of resin. With the afore described loading of flame retardant additive in the outer insulation layer, the inner insulation layer should have preferably less than about 30 parts of flame retardant additive per hundred parts by weight of resin.

A polyolefin formulated with one or more of the above described flame retardant additives, such as 120 parts per hundred parts by weight of resin (phr) of ethylene diamine phosphate and 30 phr of melamine has a dielectric constant of 3.34 and a dissipation factor of 0.0004 at 1 MHz, measured by ASTM D 1531. An insulation layer prepared from this insulation composition will not meet commercial dielectric requirements.

However, when the insulation layer is coupled with an appropriate second insulation layer, the resulting insulated conductor can meet commercial dielectric requirements. The equations (shown below) for composite dielectric constant and composite dissipation factor permit selection of an appropriate second insulation layer.

The composite dielectric constant, $\in_t$, is defined by:

$$\varepsilon_t = \frac{\varepsilon_1 \varepsilon_2 \ln\left(\frac{r_2}{r_0}\right)}{\varepsilon_2 \ln\left(\frac{r_1}{r_0}\right) + \varepsilon_1 \ln\left(\frac{r_2}{r_1}\right)}$$

where $\in_1$ and $\in_2$ are the dielectric constants of the inner and outer insulation layers, respectively, and $r_0$ is the radius of the conductor; $r_1$ is the sum of $r_0$ and the thickness of the inner insulation layer; and $r_2$ is the sum of $r_1$ plus the thickness of the outer insulation layer.

The composite dissipation factor (tan $\delta_t$) is defined as:

$$\tan \delta_t = \frac{\dfrac{\tan \delta_1}{\varepsilon_1} \ln\left(\dfrac{r_1}{r_0}\right)}{[\tan \delta_1^2 + 1]} + \dfrac{\dfrac{\tan \delta_2}{\varepsilon_2} \ln\left(\dfrac{r_2}{r_1}\right)}{[\tan \delta_2^2 + 1]}}{\dfrac{\dfrac{1}{\varepsilon_1} \ln\left(\dfrac{r_1}{r_0}\right)}{[\tan \delta_1^2 + 1]} + \dfrac{\dfrac{1}{\varepsilon_2} \ln\left(\dfrac{r_2}{r_1}\right)}{[\tan \delta_2^2 + 1]}}$$

where $\tan \delta_1$ and $\tan \delta_2$ are the dissipation factors of the inner and outer insulation layers, respectively.

To meet the composite dielectric constant of 2.6 and the composite dissipation factor of 0.005 for an insulated conductor having a 24AWG wire with diameter of 0.0212 inches and an outer insulation layer with a dielectric constant of 3.34 and a dissipation factor of 0.0004, Table 1 recites the maximum allowable dielectric properties for the inner insulation layer at each thickness. The total combined thickness of the insulation layers is 8 mils.

TABLE 1

INNER INSULATION LAYER - MAXIMUM DIELECTRIC PROPERTIES

| Thickness (mil) | Maximum DC | Maximum DF |
|---|---|---|
| 1 | 1.203 | 0.0137 |
| 2 | 1.734 | 0.0104 |
| 3 | 2.034 | 0.0085 |
| 4 | 2.227 | 0.0073 |
| 5 | 2.362 | 0.0065 |
| 6 | 2.462 | 0.0059 |
| 7 | 2.539 | 0.0054 |

Polyolefin polymer or polymer blends formulated with 25 phr ethylene diamine phosphate and 0.3 phr synergist additive, have a dielectric constant of 2.30 and a dissipation factor of 0.0004 at 1 MHz. According to Table 1, those compositions can be used as the inner insulation layer compound to meet the electrical requirements at a thickness up to 5 mils. A cable prepared with 4 twisted pairs of such insulated conductors and jacketed with commercially available plenum-rated jacket materials will meet the electrical requirements of the TIA/EIA 568 A test and the smoke and flame requirements of the NFPA 262 test.

In a preferred embodiment, the inner insulation layer, the outer insulation layer, or both insulation layers are foamed.

In a preferred, alternate embodiment, neither insulation layer has a dielectric constant greater than about 2.6 or a dissipation factor greater than about 0.005.

EXAMPLES

The following non-limiting examples illustrate the invention.

Below are the typical compositions of polyolefin polymers formulated with non-halogenated flame retardants used in the following examples of the invention.

| Compound | A (Outer Insulation) | B (Inner Insulation) | C (Inner Insulation) |
|---|---|---|---|
| Polymers | 100 phr | 100 phr | 100 phr |
| Ethylene diamine phosphate | 109 phr | 33 phr | 25 phr |
| Synergist additive | 0.3 phr | 0.3 phr | 0.3 phr |
| Antioxidants | 0.4 phr | 0.4 phr | 0.4 phr |
| Electrical Properties | | | |
| DC at 1 MHz | 3.21 | 2.59 | 2.30 |
| DF at 1 MHz | 0.00047 | 0.00042 | 0.0004 |

In these examples, a 24 AWG conductor with a diameter of 0.0212 inches is insulated with two non-halogenated polyolefins at a combined total insulation thickness of 8 mils. Compound A is the typical example of an outer insulation layer. The dielectric constant (DC) and dissipation factor (DF) of Compound A are 3.21 and 0.00047 at 1 MHz, respectively, measured by ASTM D 1531.

Table 3 recites the maximum allowable dielectric properties for the inner insulation layer at each thickness when used with Compound A as the outer insulation layer to meet the composite dielectric constant of 2.6 and the composite dissipation factor of 0.005.

TABLE 3

INNER INSULATION LAYER - MAXIMUM DIELECTRIC PROPERTIES

| Thickness (mil) | Maximum DC | Maximum DF |
|---|---|---|
| 1 | 1.303 | 0.0146 |
| 2 | 1.820 | 0.0108 |
| 3 | 2.099 | 0.0087 |
| 4 | 2.273 | 0.0074 |
| 5 | 2.393 | 0.0065 |
| 6 | 2.480 | 0.0059 |
| 7 | 2.547 | 0.0054 |

Compound B, having a dielectric constant of 2.59 and a dissipation factor of 0.00042, cannot be used as the inner insulation layer due to its high dielectric properties when Compound A is use as the outer insulation layer. However, Compound C, having a dielectric constant of 2.30 and a dissipation factor of 0.0004, can be used up to 5 mil to meet the composite electrical requirements when Compound A is used as the outer insulation layer.

The 4 twisted pairs of such insulated conductors with Compound C as the inner insulation layer and Compound A as the outer insulation layer, jacketed with the commercially available plenum-rated jacket materials, will meet the electrical requirements by TIA/EIA 568 A test and the smoke and flame requirements by NFPA 262 test.

What is claimed as new and desired to be protected by Letters Patent of the United States is:

1. A flame retardant cable comprising:
   an insulated conductor which comprises
   (a) a conductor;
   (b) an inner insulation layer surrounding the conductor; and
   (c) an outer insulation layer surrounding the inner insulation layer,
   wherein the insulated conductor having a composite dielectric constant less than or equal to 2.6 and a composite dissipation factor of less than or equal to 0.005, and wherein the inner insulation layer or the outer insulation layer has a dielectric constant greater than 2.6 or a dissipation factor greater than 0.005.

2. The cable as recited in claim 1 where the inner insulation layer, the outer insulation layer, or both insulation layers are foamed.

3. The cable as recited in claim 1, comprising four twisted pairs of the insulated conductor and a plenum-rated jacket material.

4. A flame retardant cable comprising:
an insulated conductor which comprises
(a) a conductor;
(b) an inner insulation layer surrounding the conductor; and
(c) an outer insulation layer surrounding the inner insulation layer,
wherein the insulated conductor having a composite dielectric constant less than or equal to about 2.6 and a composite dissipation factor of less than or equal to 0.005, and wherein a first polymeric composition for preparing the inner insulation layer comprises a first non-halogenated polymer and being substantially-free of halogenated flame retardant additives or antimony oxide and a second polymeric composition for preparing the outer insulation layer comprises a second non-halogenated polymer and being substantially-free of halogenated flame retardant additives or antimony oxide.

5. The cable as recited in claim 4, wherein the first polymeric composition further comprises non-halogenated flame retardant additives in an amount no more than 30 parts per hundred parts of the first non-halogenated polymer by weight and the second polymeric composition further comprises non-halogenated flame retardant additives in an amount between 100 to 300 parts per hundred parts by weight of the second non-halogenated polymer by weight.

6. The cable as recited in claim 5, wherein the non-halogenated flame retardant additives are selected from the group consisting of ethylene diamine phosphate, melamine, melamine pyrophosphate, melamine phosphate, ammonium polyphosphate, melamine polyphosphate, calcium carbonate, talc, clay, organo-modified clay, calcium hexaborate, alumina, titanium oxides, carbon nanotubes, zinc borate, wollastonite, mica, silicone polymers, phosphate esters, hindered amine stabilizers, melamine octomolybdate, ammonium octomolybdate, expandable graphite, frit, hollow glass beads, and mixtures thereof.

7. The cable as recited in claim 6, wherein the insulated conductor has two layers which have a composite dielectric constant ($\varepsilon_t$) and a composite dissipation factor (tan $\delta_t$) defined by the following $$\varepsilon_t = \frac{\varepsilon_1 \varepsilon_2 \ln\left(\frac{r_2}{r_0}\right)}{\varepsilon_2 \ln\left(\frac{r_1}{r_0}\right) + \varepsilon_1 \ln\left(\frac{r_2}{r_1}\right)}$$

and $$\tan \delta_t = \frac{\frac{\tan \delta_1}{\varepsilon_1} \ln\left(\frac{r_1}{r_0}\right)}{[\tan \delta_1^2 + 1]} + \frac{\frac{\tan \delta_2}{\varepsilon_2} \ln\left(\frac{r_2}{r_1}\right)}{[\tan \delta_2^2 + 1]} \bigg/ \frac{\frac{1}{\varepsilon_1} \ln\left(\frac{r_1}{r_0}\right)}{[\tan \delta_1^2 + 1]} + \frac{\frac{1}{\varepsilon_2} \ln\left(\frac{r_2}{r_1}\right)}{[\tan \delta_2^2 + 1]}$$

where $\varepsilon_1$ and $\varepsilon_2$ are the dielectric constants of the inner and outer insulation layers, respectively, and $r_0$ is the radius of the conductor; $r_1$ is the sum of $r_0$ and the thickness of the inner insulation layer; and $r_2$ is the sum of $r_1$ plus the thickness of the outer insulation layer; and where tan $\delta_1$ and tan $\delta_2$ are the dissipation factors of the inner and outer insulation layers, respectively.

* * * * *